(12) United States Patent
Hong et al.

(10) Patent No.: US 10,758,740 B2
(45) Date of Patent: Sep. 1, 2020

(54) SYSTEM, APPARATUS AND METHOD FOR TRANSIENT ELECTRIC FIELD DETECTION AND DISPLAY

(71) Applicant: University of Maryland, Baltimore, Baltimore, MD (US)

(72) Inventors: Liyi Elliot Hong, Ellicott City, MD (US); Fow-Sen Choa, Ellicott City, MD (US)

(73) Assignees: University of Maryland, Baltimore, Baltimore, MD (US); University of Maryland, Baltimore County, Baltimore, MD (US)

( * ) Notice: Subject to any disclaimer, the term of this patent is extended or adjusted under 35 U.S.C. 154(b) by 432 days.

(21) Appl. No.: 15/403,348

(22) Filed: Jan. 11, 2017

(65) Prior Publication Data

US 2017/0197087 A1 Jul. 13, 2017

Related U.S. Application Data

(60) Provisional application No. 62/277,148, filed on Jan. 11, 2016.

(51) Int. Cl.
*A61N 2/00* (2006.01)
(52) U.S. Cl.
CPC .................. *A61N 2/006* (2013.01)
(58) Field of Classification Search
CPC ............ A61N 2/02; A61N 2/08; A61N 2/008
See application file for complete search history.

(56) References Cited

U.S. PATENT DOCUMENTS

| | | | | |
|---|---|---|---|---|
| 6,255,815 B1* | 7/2001 | Davey | ................. | G01R 33/028 324/202 |
| 2003/0004392 A1* | 1/2003 | Tanner | ................... | A61B 5/055 600/9 |
| 2003/0050527 A1* | 3/2003 | Fox | .......................... | A61N 2/02 600/13 |
| 2004/0077921 A1* | 4/2004 | Becker | .................. | A61N 2/008 600/9 |
| 2006/0122496 A1* | 6/2006 | George | ................. | A61B 5/055 600/424 |
| 2006/0152427 A1* | 7/2006 | Ueda | ........................ | H01Q 7/08 343/788 |

(Continued)

*Primary Examiner* — Alvaro E Fortich
(74) *Attorney, Agent, or Firm* — Whiteford, Taylor & Preston, LLP; Gregory M. Stone

(57) ABSTRACT

Disclosed are systems, devices and methods for detecting and measuring TMS-induced electrical fields. In accordance with certain aspects of an embodiment of the invention, a TMS sensor probe is provided having a field detector, a first electrical connection connecting the field detector to either a power source or a processor, and a second electrical connection connecting the field detector to a processor. The field detector is configured to measure a characteristic of a TMS-induced electrical field at the location of the field detector, and the processor is configured to receive the measured characteristic of the induced electrical fields and display a human-readable depiction of a calculated induced electrical field. A system using such a sensor probe to calibrate a TMS-induced electrical field is also provided, including the foregoing sensor probe, and a magnetic field generator.

12 Claims, 13 Drawing Sheets

(56) References Cited

U.S. PATENT DOCUMENTS

| | | | | |
|---|---|---|---|---|
| 2007/0273374 A1* | 11/2007 | Haase | ............... | G01R 33/381 |
| | | | | 324/308 |
| 2007/0282189 A1* | 12/2007 | Dan | ............... | A61B 5/0059 |
| | | | | 600/407 |
| 2009/0012655 A1* | 1/2009 | Kienman | ............... | A61M 1/28 |
| | | | | 700/300 |
| 2013/0307763 A1* | 11/2013 | Galluppi | ............... | G01R 29/0892 |
| | | | | 345/156 |
| 2014/0357935 A1* | 12/2014 | Ilmoniemi | ............... | A61N 2/006 |
| | | | | 600/13 |
| 2017/0090613 A1* | 3/2017 | Mei | ............... | G06F 3/044 |
| 2017/0108539 A1* | 4/2017 | Connell | ............... | G01R 19/0092 |

\* cited by examiner

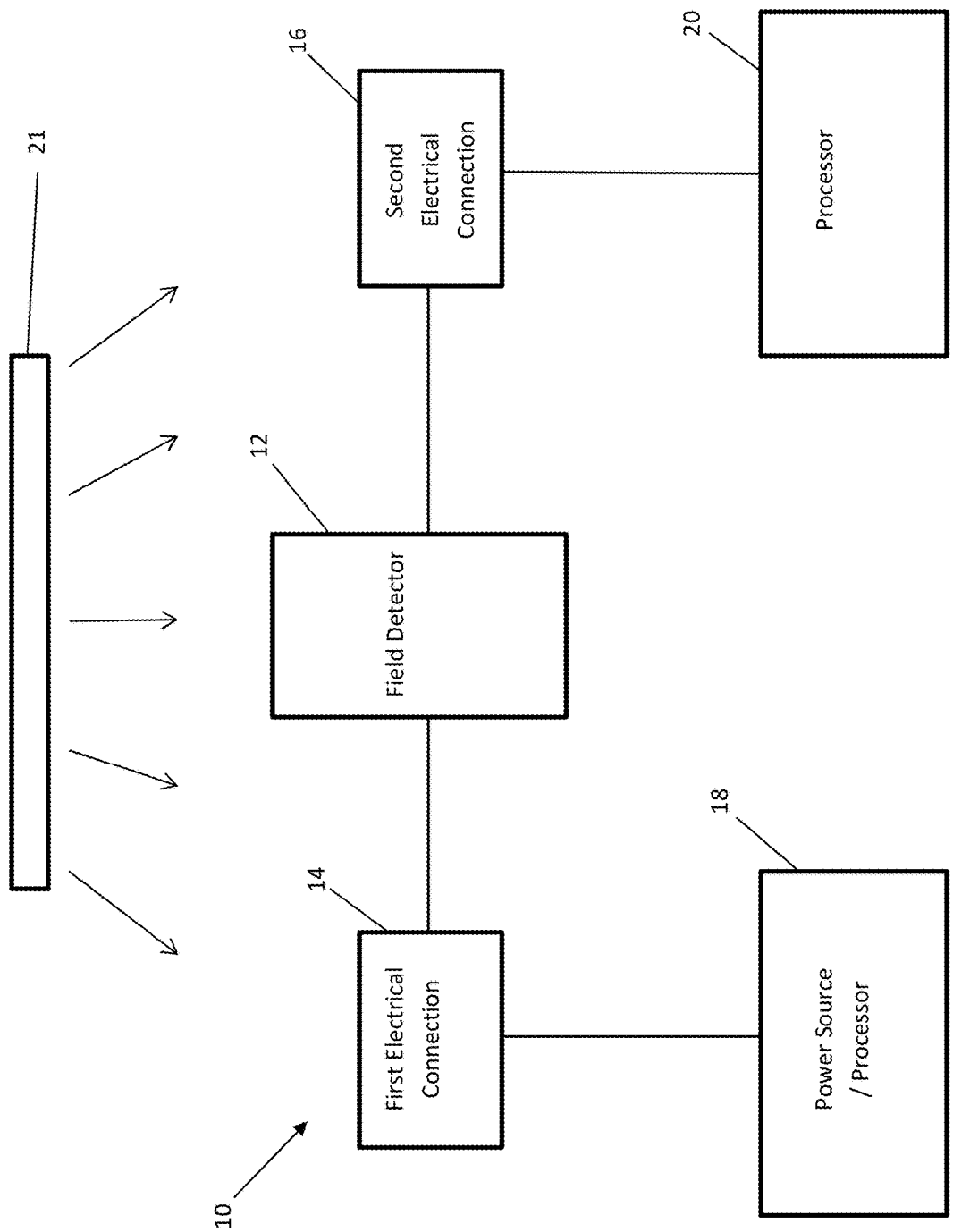

SYSTEM, APPARATUS AND METHOD FOR TRANSIENT ELECTRIC FIELD DETECTION AND DISPLAY

CROSS-REFERENCE TO RELATED APPLICATION

This application is based upon and claims the benefit of U.S. Provisional Patent Application Ser. No. 62/277,148 entitled "Transient Electric Field Sensor Probe," filed with the U.S. Patent and Trademark Office on Jan. 11, 2016 by the inventors herein, the specification of which is incorporated herein by reference in its entirety.

FIELD OF THE INVENTION

The present invention relates generally to systems, devices, and methods for detecting transcranial magnetic stimulation (TMS). More particularly, the present invention relates to probes, and to systems and methods of using such probes, for detecting TMS and calibrating TMS devices.

BACKGROUND OF THE INVENTION

There is increasing interest in using transcranial magnetic stimulation (TMS) as a treatment tool for various neurological and psychiatric disorders, including migraine, stroke, Parkinson's disease, dystonia, tinnitus, and depression. TMS is a noninvasive method that uses a weak transient magnetic field-induced current to stimulate regions of the brain. The magnetic pulse created by a magnetic field generator easily passes through the skull and induces small electrical currents to be generated that stimulate nerve cells in the targeted brain region. The United States Food and Drug Administration (FDA) has approved TMS as treatment for depression and migraine headaches. TMS is also used as a diagnostic tool for motor neuron diseases with spinal cord excitation.

In order to meet the need for improved TMS devices that provide for deeper organ and brain stimulation, new TMS tools will require higher pulse power and better focusing capabilities to combat field divergence caused by longer operational distances. Developing such focused TMS requires extensive testing before it can be applied to animals and then humans. Even after new and more focused TMS devices are developed, they will require regular calibration and maintenance to ensure precision in focusing and intensity. Accordingly, there is a need for measurement tools, such as sensor probes and systems employing sensor probes and phantoms (e.g., brain phantoms) to detect the TMS-induced field and current, their focality, intensity, and temporal and spatial characteristics.

SUMMARY OF THE INVENTION

Provided herein are systems, devices and methods for detecting and measuring TMS-induced electrical fields. In accordance with certain aspects of an embodiment of the invention, a TMS sensor probe is provided having a field detector, a first electrical connection connecting the field detector to either a power source or a processor, and a second electrical connection connecting the field detector to a processor. The field detector is configured to measure a characteristic of a TMS-induced electrical field at the location of the field detector, and the processor is configured to receive the measured characteristic of the induced electrical field and display a human-readable depiction, such as a visual model, of a calculated induced electrical field. A system using such a sensor probe to calibrate a TMS field is also provided, including the foregoing sensor probe, and a magnetic field generator.

In accordance with a particular exemplary configuration, a TMS sensor probe includes a resistor probe configured to detect TMS-induced electrical fields, including a resistor having a first electrical lead and a second electrical lead, one of a power source or a processor connected to the first electrical lead, and a processor in communication with the second electrical lead, wherein the processor is configured to receive changes in voltages across the resistor and convert the changes into a human readable depiction of an electrical field. The processor may communicate with a monitor that displays the human readable depiction of the measured electrical field.

In accordance with another particular exemplary configuration, a TMS sensor probe includes a coil inductor probe having an electrical wire having a first portion, a second portion, and a coil between the first portion and the second portion, wherein the end of the first portion is in communication with one of a power source or a processor, and wherein the end of the second portion is connected to a processor that is configured to determine the envelope of the measured pulse field of a TMS-induced electrical field, and to convert the envelope into a human readable depiction of an electrical field. The processor may communicate with a monitor that displays the human readable depiction of the measured electrical field.

In accordance with yet another particular exemplary configuration, a TMS sensor probe includes a directional electrical field probe having a first coil made of magnetic material and a second coil made of electrical conductive material, wherein the second coil has a first end, a second end, and a middle portion, wherein the middle portion is coiled around at least a portion of the first coil, wherein the first end communicates with one of a power source or a processor, and wherein the second end communicates with a processor that is configured to detect a change in voltage across the second coil and to convert the change in voltage into a human readable depiction of an electrical field. Once again, the processor may communicate with a monitor that displays the human readable depiction of the measured electrical field.

Methods are also provided for simultaneously measuring vector electrical and magnetic field distribution using a TMS sensor probe configured as described herein. Such measurements may be verified with the electric field and magnetic field relationship as described by the Maxwell equation.

BRIEF DESCRIPTION OF THE DRAWINGS

The numerous advantages of the present invention may be better understood by those skilled in the art by reference to the accompanying figures in which:

FIG. 1 is a schematic view of a TMS sensor probe in accordance with certain aspects of an embodiment of the invention.

DETAILED DESCRIPTION OF THE PREFERRED EMBODIMENTS

Figure 2A:
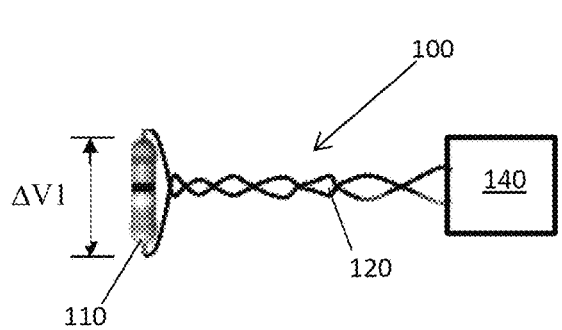
FIG. 2(a) shows an exemplary configuration for a resistor type TMS sensor probe in accordance with certain aspects of the invention.

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form. Further, it should be understood that the figures are not drawn to scale and in some instances details that are not necessary for the understanding of the present invention are omitted such as common methods of manufacturing.

Systems, devices and methods are provided for detecting characteristics of TMS electrical fields and displaying a human-readable depiction, such as a visual model, of a calculated induced electrical field, and for calibrating TMS devices. The invention is described with reference to the drawings in which like references are labeled with like numerals. The relationship and functioning between the various elements are better understood by reference to the figures. However, the embodiments described herein are examples only and the invention is not limited to those specifically described or depicted in the figures. It should be understood that the figures are not drawn to scale and in some instances details that are not necessary for the understanding of the present invention are omitted such as common methods and manufacturing. Furthermore, it should be understood that the invention described herein is generally described in terms of transcranial magnetic stimulation probes and related systems, and methods of their use. However, it should be understood that the devices, systems and methods of the present invention may be used for a wide range of uses including serving as a probe and calibrating device for other areas of the body. One having ordinary skill in the art would recognize minor changes that would be necessary to adapt the system for different uses. These modifications should be considered part of the invention because they do not deviate from its overall spirit.

The basic principle of a TMS probe according to certain aspects of the invention is to measure the induced electrical field by recording the potential difference between two points in space and dividing it by the distance between the two points. The following description includes some devices and methods to accomplish this. However, one skilled in the art would readily recognize other configurations and methods in light of the teachings herein. Such configurations and methods should be considered part of the present invention as they do not deviate from the spirit of the present invention. To achieve the measurement, the following description provides a few different implementations.

FIG. 1 provides a schematic view of a TMS sensor probe in accordance with certain aspects of an embodiment of the invention. The TMS sensor probe, shown generally at 10, comprises a field detector 12 positioned between and in electrical communication with a first electrical connection 14 and a second electrical connection 16. Field detector 12 is configured to measure a characteristic of an induced electrical field at a location of field detector 12, which induced electrical field results from a magnetic field generated by a magnetic field generator 21. First electrical connection 14 is likewise attached to and in electrical communication with a power source 18 or processor 20, and second electrical connection 16 is attached to and in electrical communication with a processor 20. At least in configurations in which field detector 12 need not be powered in order to detect the subject characteristic of the induced electrical field, power source/processor 18 and processor 20 may be a single, physical unit. Likewise, even in those configurations in which field detector 12 is to be powered by a power source 18, power source 18 and processor 20 may share a common physical housing. In any case, processor 20 is configured to receive from second electrical connection 16 a signal representative of the measured characteristic of the induced electrical field, and to generate and display a human-readable depiction of a calculated induced electrical field, which in turn may be used to calibrate the field generated by magnetic field generator 21.

Figure 2B:
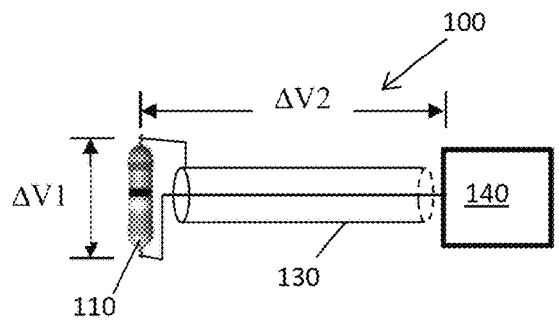
FIG. 2(b) shows another exemplary configuration for a resistor type TMS sensor probe in accordance with certain aspects of the invention.

FIGS. 2(*a*) and 2(*b*) depict exemplary resistor probes (shown generally at 100) in accordance with certain aspects of an embodiment. Each resistor probe 100 includes a resistor 110 forming the field detector 12, and a wire connection, which can be either a twist pair 120 or a coaxial cable 130 forming the first and second electrical connections or leads. Thus, each of twist pair 120 and coaxial cable 130 form a first electrical lead as the first electrical connection 14, and a second electrical lead as the second electrical connection 16. In each configuration, the voltage drop change ΔV1 across the resistor 110 is proportional to the TMS-induced electrical field at the location of resistor 110. Preferably the voltage drop or change ΔV2 of the wire connection is minimized as much as practical for a given application. The measured probe output signal is recorded by a processor or other analytical instrument 140 (serving as processor 20 of FIG. 1). The measured probe output signal includes contributions from the voltage drop ΔV1 of the resistor and voltage drop ΔV2 of the wiring. By placing the resistor probe 100, and more particularly resistor 110, at a location with respect to field generator 21 that coincides with the intended site of TMS, resistor 110 may be used to measure the induced electric field at the exact intended site of TMS. The processor 140 is configured to receive voltage drops ΔV1 across the resistor and convert the changes into a visual model of the induced electrical field. The resistor 110 may have a resistance value as low as near zero and has no maximum. The first and second electrical leads of resistor probe 100 may be made of any conductive wire. However, in certain embodiments the first and second electrical leads of resistor probe 100 are made of an insulated 32 gauge copper wire. The terminal change in voltage ΔV is calculated using Formula 1:

$$\Delta V = \Delta V1 + \Delta V2, \Delta V1 = \int_0^L E\, dl, \Delta V2 = \text{wiring pickups} \qquad \text{Formula 1:}$$

Figure 3:
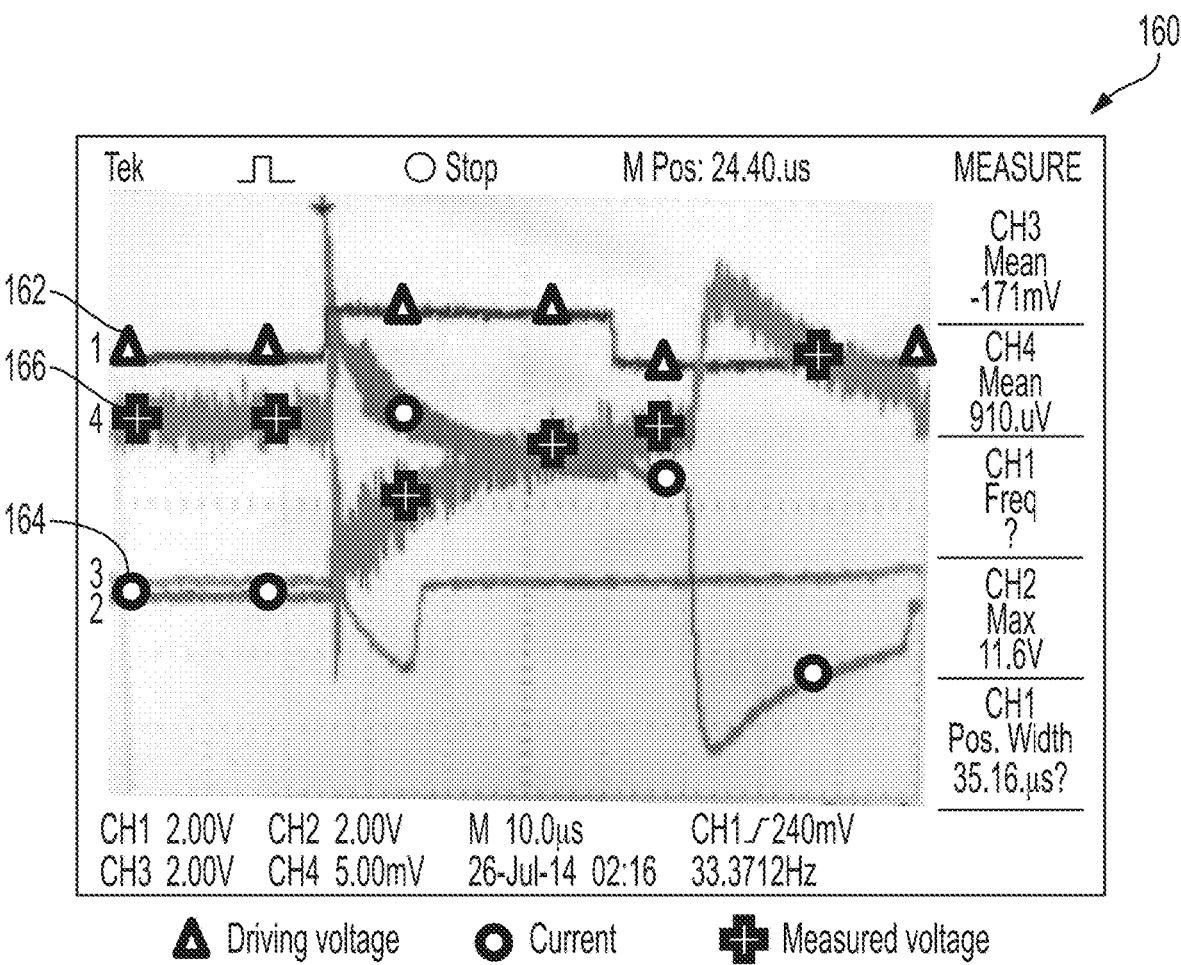
FIG. 3 shows sample readings from a resistor type TMS sensor probe of FIGS. 2(a) and 2(b).

As shown in Formula 1, the resistance value of resistor 110 is not important. The integration path length L is the only contributing factor if the induced electrical field E is fixed. However, characteristics of a measurement loop, which includes the resistor 110, the twist pair 120 or the coaxial cable 130, and the input impedance of the processor 140, must satisfy Kirchhoff's circuit laws. Experimental results in the examples below illustrate that the output signal has a low amplitude if the resistance value of resistor 110 is small, and the amplitude of the output signal is large if the resistance value of resistor 110 is large, but the resistor probe would also detect a significant amount of ambient noise. An extreme case is where R=∞, in which case the resistor probe 100 effectively functions as two electrodes floating in the air detecting potentials at their locations. The resistance value of resistor 110 is preferably approximately between 2 kohms and 3 kohms to provide an output signal amplitude that is approximately 5 mV, which is reasonably sufficient to overcome signal noise that has an amplitude at an approximately same order as the output signal. The measured results of such a configuration are depicted in representative display 160 of FIG. 3. As shown in FIG. 3, the driving voltage 162 (shown in yellow) and current 164 (shown in blue) are sent into the magnetic field generator 21, such as a typical FIG. 8 TMS unit, in turn generating the measured voltage output from the probe 166 (shown in green).

Such resistor probes 100 have the advantage of simplicity, but their output signal is weak and the resistor probe also detects compatible and higher amplitude surrounding noises from the first and second electrical leads, even if the first or second electrical lead is the twisted pair 120. Further, the resistor probe 100 is not directionally sensitive to the measured electric field in this configuration.

Figure 4A:
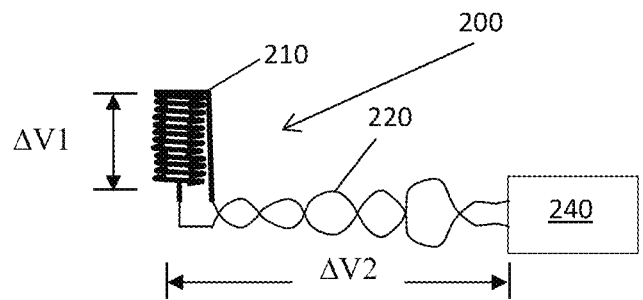
FIG. 4(a) shows an exemplary configuration for a coil inductor type TMS sensor probe in accordance with certain aspects of the invention.
Figure 4B:
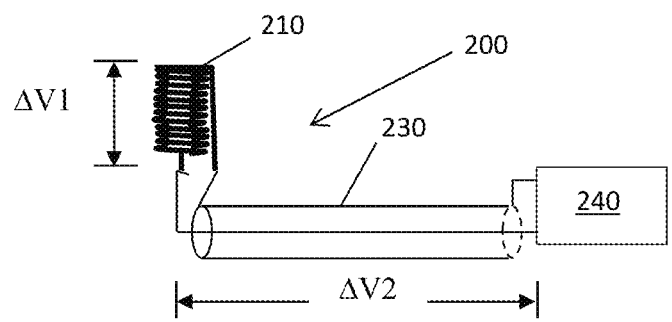
FIG. 4(b) shows another exemplary configuration for a coil inductor type TMS sensor probe in accordance with certain aspects of the invention.

Next, FIGS. 4(*a*) and 4(*b*) depict exemplary coil inductor probes (shown generally at 200) in accordance with certain aspects of an embodiment. Each coil inductor probe 200 includes an electrical coil 210 forming the field detector 12, and a wire connection, which can be either a twist pair 220 or a coaxial cable 230 forming the first and second electrical connections. Thus, each of twist pair 220 and coaxial cable 230 form a first electrical lead as the first electrical connection 14, and a second electrical lead as the second electrical connection 16. The measured probe output is sent to a processor 240 (serving as processor 20 of FIG. 1), which is configured to detect the envelope of the measured pulse field of a TMS-induced electrical field. The coil inductor probe 200 may be made of any known electricity conducting wire. However, in a particularly preferred configuration, an insulated copper wire is typically used. Due to the parasitic capacitance in the circuit and particularly along the connection wire, RLC oscillations (resistance (R), inductance (L), capacitance (C)) can be observed. L is dominated by the given inductor and C is dominated by the parasitic capacitance between the wires with difference polarity. The oscillation frequency is shown in Formula 2 and inversely proportional to the square root of the LC product. To eliminate the oscillation, one may change the input impedance of the measurement instrument from 1 Mohm to 50 ohm. As shown in Formula 2 below, the damping constant τ is inversely proportional to the RLC circuit resistance R. With a large RL charging time, the circuit removed all the LC oscillations and the circuit detects only the envelope of the TMS-induced field.

$$\omega = 1/(LC)^{1/2}, \tau = L/R \qquad \text{Formula 2:}$$

Depending on the inductance value, the output of the coil inductor probe 200 can be three to four orders of magnitude higher than the resistor probe 100 configuration discussed above. Furthermore, most of the ambient noises, such as 60 Hz interference, are low frequency signals. At low frequency the inductor behaves like a short circuit and the inductor does not detect these low frequency signals well. The coil inductor probe 200 detects the TMS-induced signal in proportion to the number of coil winding turns to output a larger amplitude signal. The same TMS signal can produce only a signal between 5 mV and 10 mV with the resistor probe 100 and with a significant amount of noise, but the inductor probe 200 can output a signal having an amplitude on the order of a few volts with a negligible amount of noise.

Figure 5:
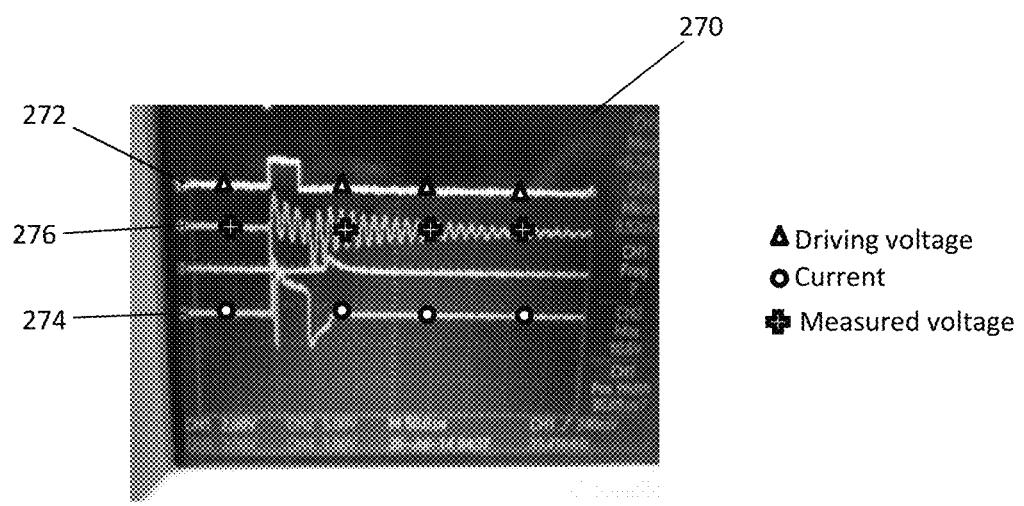
FIG. 5 shows sample readings from a coil inductor type TMS sensor probe of FIGS. 4(a) and 4(b).
Figure 6:
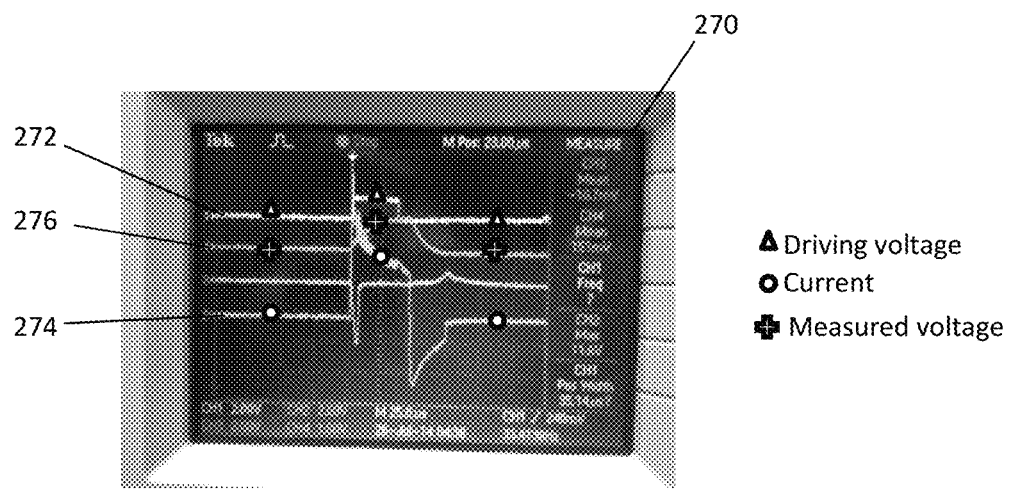
FIG. 6 shows an output measurement of a coil inductor type TMS sensor probe of FIGS. 4(a) and 4(b) when the envelope of the measured pulse is extracted.

Even more, the coil inductor probe 200 is high directional. It will measure an electric field projected to one direction only and provides a basic building block for a 3-D electric field probe. FIG. 5 depicts an exemplary monitor 270 that depicts the driving voltage 272 (yellow trace), current 274 (blue trace), and measured voltage output 276 (green trace) from the coil inductor probe 200. The background noise pickup from the ambient environment is generally negligible. The envelope of the measured pulse field can be measured by reducing the input impedance of the oscilloscope, as depicted in FIG. 6. The 3-D output signal recorded from the coil inductor probe 200 represents dB/dt (or −∇×E) and not the electric field itself. Processor 240 obtains the electric field distributions by further processing the recorded signal distribution and inversely calculating the electric field by using methods known to those of ordinary skill in the art.

Figure 7:
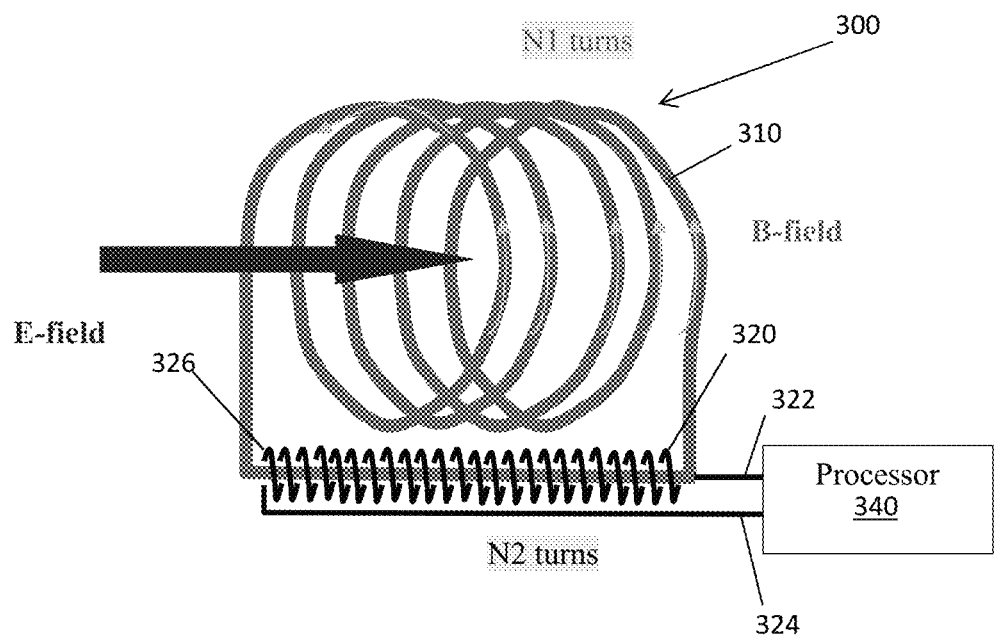
FIG. 7 is a schematic view of an exemplary configuration of a directional TMS sensor probe in accordance with certain aspects of the invention.

Next, FIG. 7 depicts an exemplary directional field probe (shown generally at 300) in accordance with certain aspects of an embodiment. Directional field probe 300 includes a first coil 310 made of magnetic material and a second coil 320 made of electrical conductive material. Each of the first coil 310 and the second coil 320 has a number of coil turns or loops. Second coil 320 has a first end 322 forming the first electrical connection 14, and a second end 324 forming the second electrical connection 16. Second coil 320 also has a middle portion 326, which middle portion 326 is coiled around at least a portion of first coil 310. Middle portion 326 of second coil 320 in combination with first magnetic coil 310 forms the field detector 12. Further, each of first end 322 and second end 324 of second coil 320 communicate with processor 340 (serving as processor 20 of FIG. 1), which is configured to detect a change in voltage across the second coil 320. Second coil 320 may be composed of any nonmagnetic electrically conductive wires. The number of coil turns of magnetic first coil 310 may range from one to several thousand so long as the amplitude of the output signal to the processor 340 can be effectively increased approximately proportionally with the number of turns. In certain configurations, the number of coil turns of magnetic coil 310 is approximately between 10 coil turns and 20 coil turns. The number of coil turns of second coil 320 may range from approximately 1 coil turn to about 10,000 coil turns; in certain configurations, the number of coil turns of second coil 320 is about 1000. The electrical second wire coil 320 may cover a portion of the magnetic first coil 310, as depicted in FIG. 7, or alternatively may cover the entire magnetic first coil 310, as depicted in FIG. 8 for more general applications.

Figure 8:
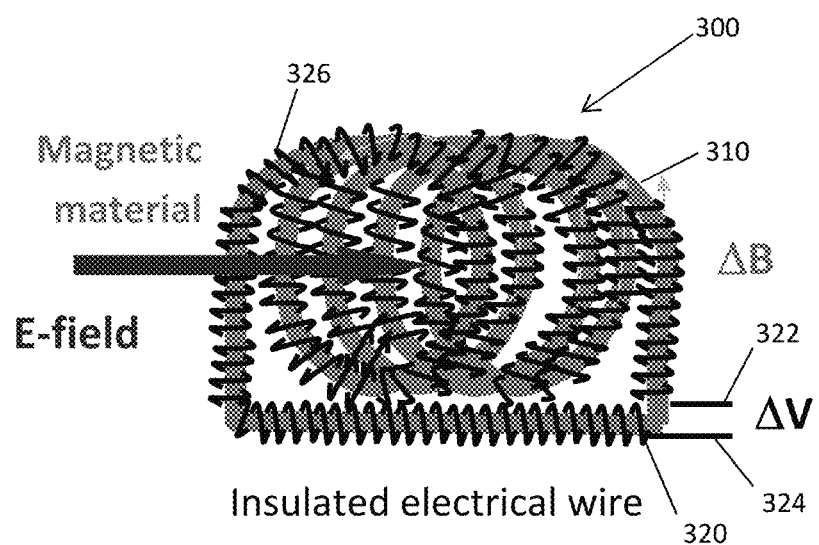
FIG. 8 is a schematic view of another exemplary configuration of a directional TMS sensor probe in accordance with certain aspects of the invention.
Figure 9:
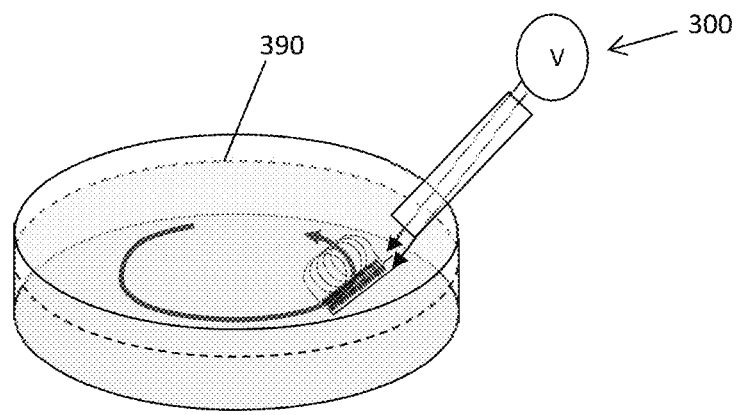
FIG. 9 is a schematic view of a directional TMS sensor probe of FIGS. 8 and 9 in a brain phantom.

The directional field probe 300 shown in FIG. 8 will detect both dB/dt and the electric field. The directional field probe 300 shown in FIG. 7 only detects the electric field. To explain why, the directional field probe 300 shown in FIG. 7 can be examined. When a dB/dt field is building up, it will induce a current flowing in the magnetic material first coil 310. The induced current will then create a magnetic field circulating the straight part of the magnetic material first coil 310. Such a magnetic field will not induce any current or electrical field in the circuit formed by second electrical coil 320.

Figure 10:
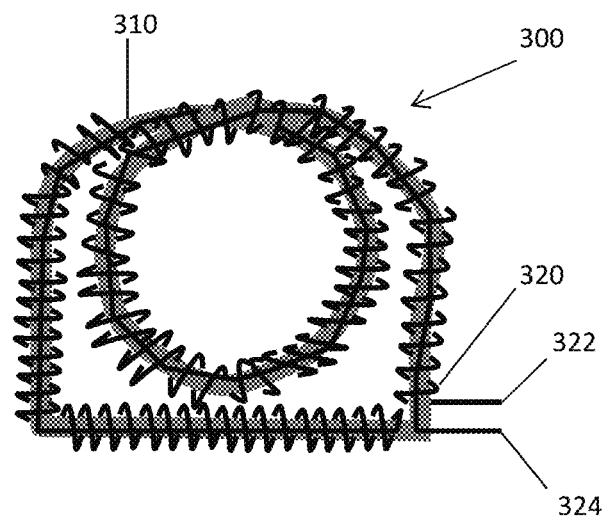
FIG. 10 is a schematic view of another exemplary configuration of a directional TMS sensor probe in accordance with certain aspects of the invention, wherein the second end of the coil that is made of an electrical conductive material is routed back to the first end.

FIG. 10 illustrates a modification to the directional field probe 300 illustrated in FIGS. 7 and 8. Here, the second end 324 of second coil 320 is routed back to the first end 322. This configuration prevents the magnetic field from passing through the area formed by second coil 320. However, the electrical field can pass through one or more cross-sectional areas formed by the magnetic first coil 310. The magnetic flux (dB/dt) creates the induced current and terminal voltage ΔV in the copper wire of second coil 320. When the winding of the second coil 320 is not symmetric forwards and backwards the net magnetic flux will produce the induced current and terminal voltage ΔV at the first end 322 and second end 324 that is proportional to the electrical field.

In certain configurations, the first coil 310 may be formed of a nonmagnetic and nonelectrically conductive material. Such a configuration is a high saturation field probe and prevents the directional field probe 300 from magnetically saturating when the induced magnetic field has a sufficiently high amplitude. However, a high saturation field probe may have a low sensitivity to the magnetic field. The configuration of FIG. 10 may also be implemented as a high sensitivity probe, wherein first coil 310 is made of a magnetic oxide material. In this particular configuration, it is important to avoid inducing the current induced inside the magnetic first coil 310, which will affect detection of the field distribution.

Figure 11:
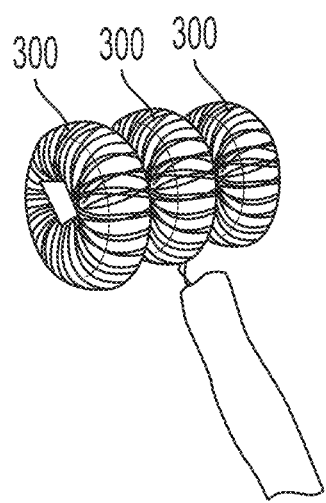
FIG. 11 shows an exemplary configuration for a staked TMS sensor probe in accordance with certain aspects of the invention.

FIG. 11 illustrates a stacked probe comprised of multiple directional field probes 300. Here, two or more directional field probes 300, configured as described above with reference to FIGS. 7, 8, and 10, are connected. Stacking multiple directional field probes 300 can increase both electric field measurement sensitivity and directivity because sensitivity linearly increases with the number of coil turns and directivity measurement also improves with the number of coil turns that are stacked. While there is generally no limit to the number of coil turns that can be stacked, locality of the probe is reduced as the number of coil turns increases.

The TMS sensor probes as described above may form part of a system used to measure and calibrate TMS devices, which system may be used in place of a brain phantom 390. An exemplary composition of brain phantom 390 is salt water and carboxymethyl cellulose. However, other compositions of phantoms are known in the art and should be considered within the scope of the instant invention.

EXAMPLES

Figure 12:
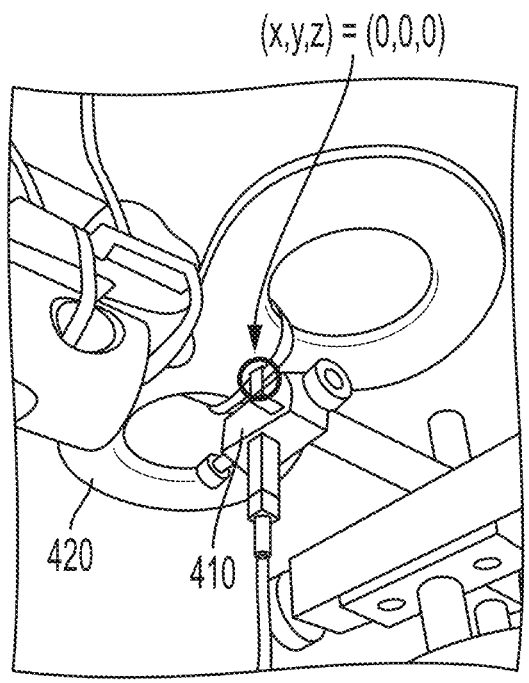
FIG. 12 shows an exemplary configuration for measuring the DC static 3D magnetic field distribution from a commercially available magnetic field generator using a commercially available 3D magnetic field measurement instrument for purposes of comparison with TMS sensor probes according to certain aspects of the invention.
Figure 13:
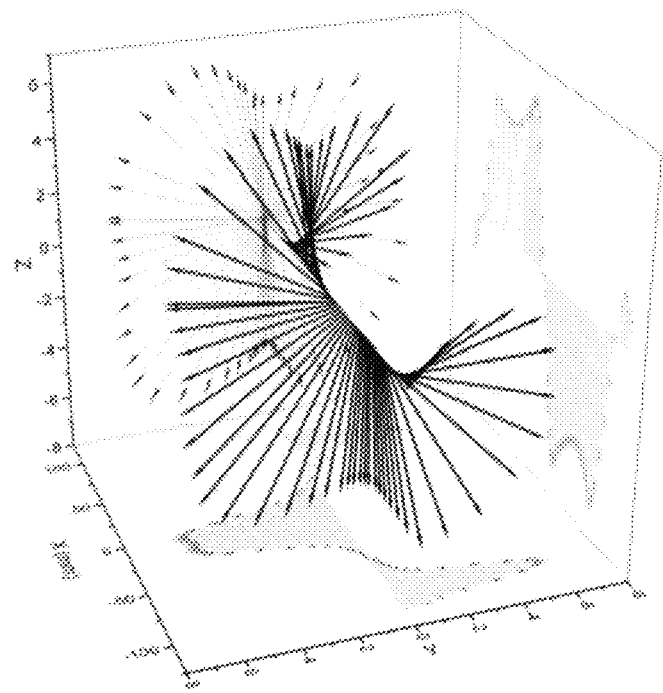
FIG. 13 shows measured results of DC static 3D magnetic field distribution from the magnetic field generator of FIG. 12.
Figure 14:
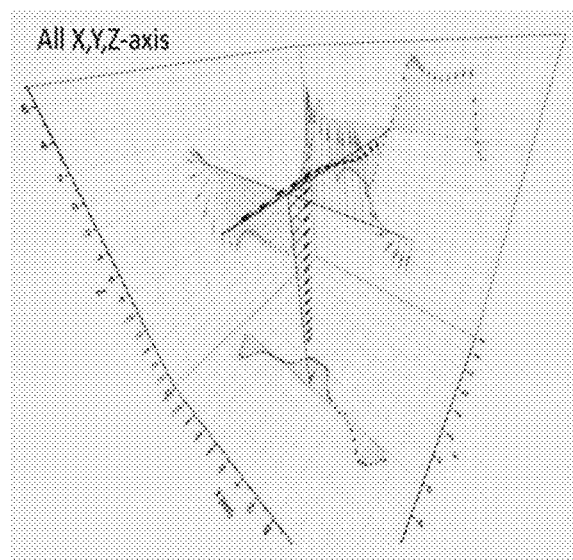
FIG. 14 shows additional measured results of DC static 3D magnetic field distribution from the magnetic field generator of FIG. 12.

FIG. 12 depicts an exemplary measurement setup. A commercially available 3-D direct current (DC) magnetic field measurement instrument 410 was used to measure a magnetic field created by a magnetic field generator, such as a commercial Figure-8 TMS stimulator 420 when a DC current is flowing through the unit. FIGS. 13 and 14 depict measured results of the 3D DC static magnetic field distribution produced by magnetic field generator 420, which can be used to calibrate the directivity, the measured dB/dt vectors, and the e vector field.

Example 1: Resistor Probe

Figure 15:
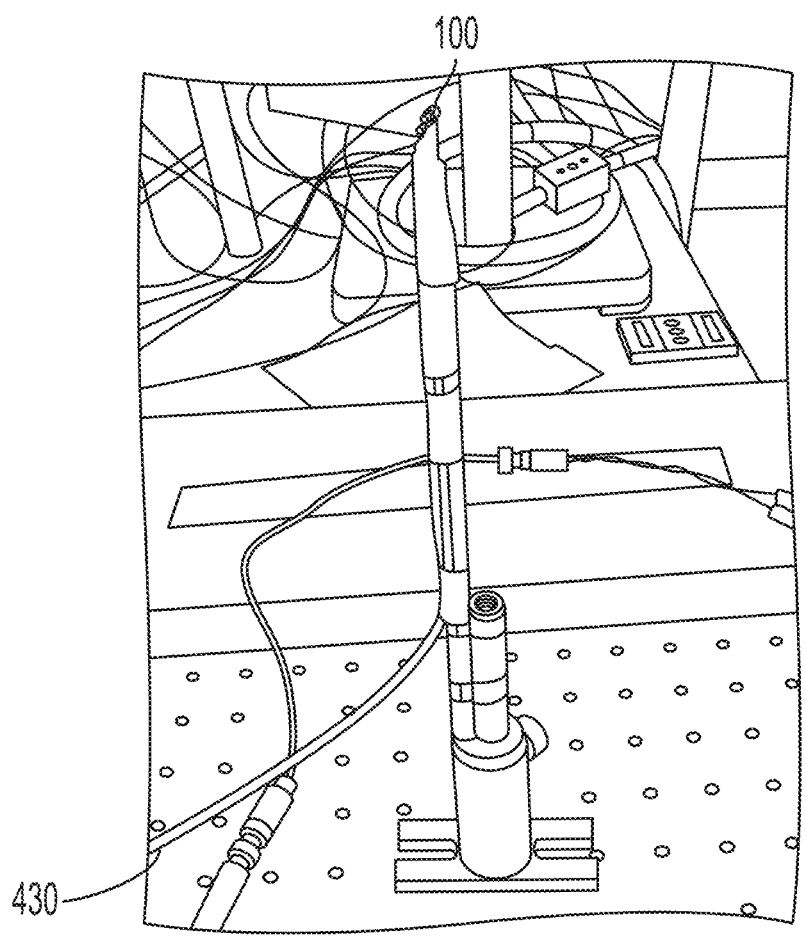
FIG. 15 shows an exemplary test configuration of a TMS sensor probe configured in accordance with certain aspects of the invention.
Figure 16:
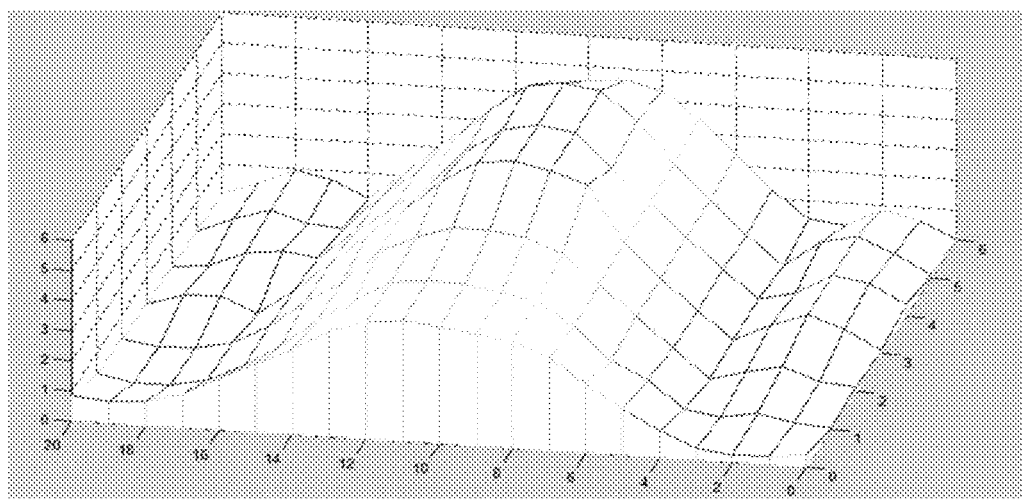
FIG. 16 depicts sample measured results of DC static 3D magnetic field distribution using the direct measurement TMS sensor probe shown in FIG. 15.

In a preliminary experiment, the same commercial Figure-8 TMS stimulator shown in FIG. 12 is driven by a pulse generator and pulse amplifier system to create magnetic pulses. FIG. 15 illustrates resistor probe 100, as described above, placed in the magnetic field produced by the pulse generator to measure the magnetic pulse-induced electric field. Coaxial cable 430 connects the resistor 110 to the measurement instrument 410. FIG. 16 illustrates the resultant measured field distribution that generally matches the field strength map of a typical Figure-8 TMS stimulator 420. For example, highest amplitude region of the induced magnetic field is generally directly beneath the middle part of the Figure-8 TMS stimulator 420.

Example 2: Directional Electrical Field Probe

Figure 17A:
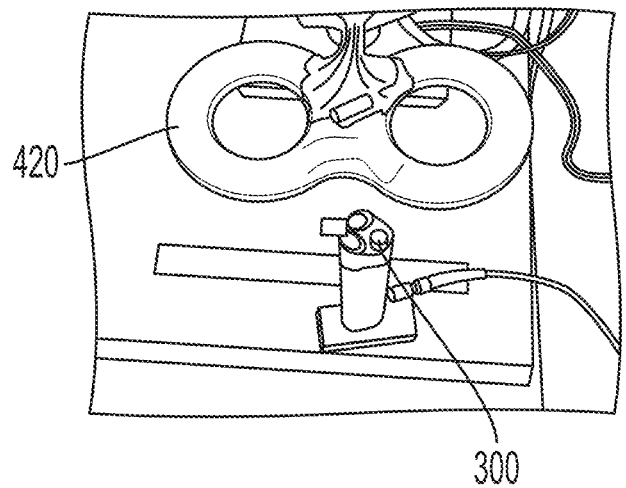
FIGS. 17(a) and (b) illustrate an exemplary implementation of a 1-D directional electrical field probe.
Figure 17B:
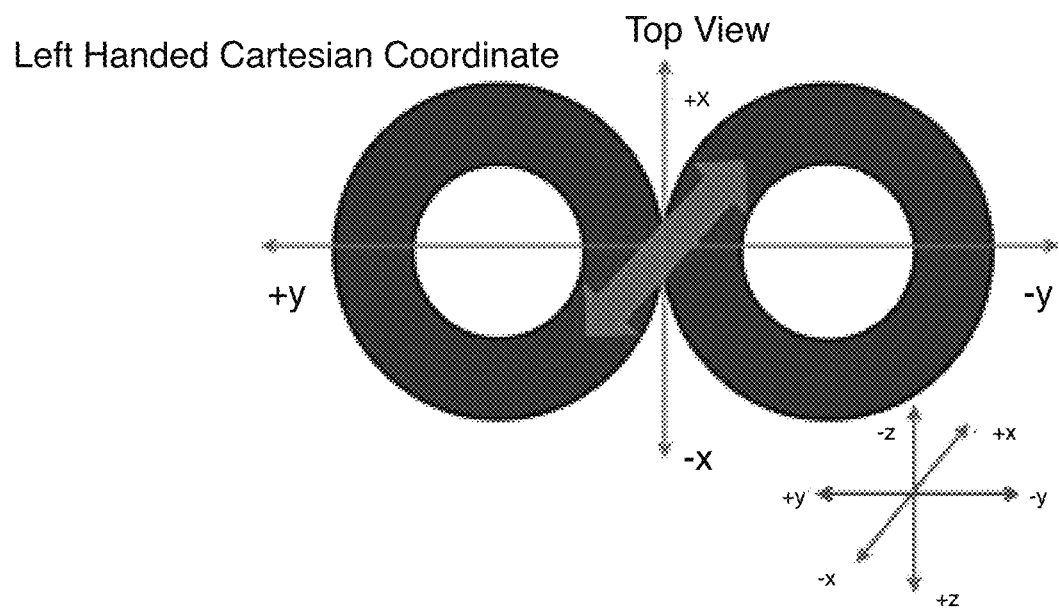
Figure 18A:
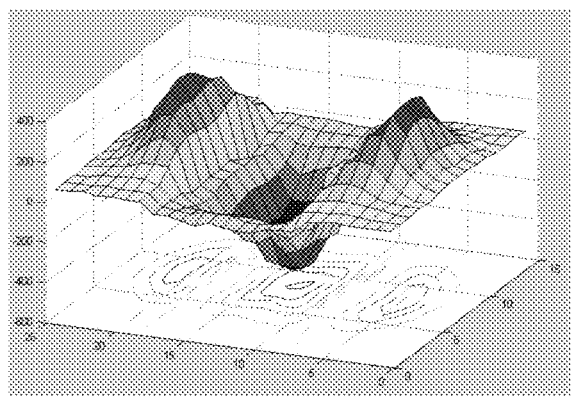
FIGS. 18(a), 18(b), and 18(c) depict sample data using the directional TMS sensor probe according to certain aspects of the invention when the probe is along the x, y, and z directions.
Figure 18B:
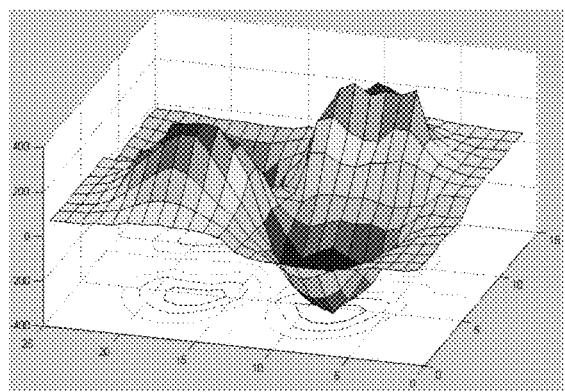
Figure 18C:
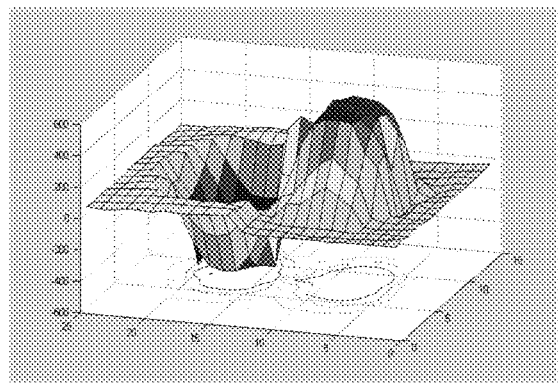

FIG. 17(a) shows an exemplary implementation of a 1-D directional electrical field probe 300, as described above. Commercial inductors limit the size of the inductor, although smaller inductors would be preferred for use in the probes 300 of the present invention. The x, y, z coordinates are defined according to FIG. 17(b). FIGS. 18(a) through 18(c) depict sample data using the directional electrical field probe 300 described above when the probe is along the x, y, and z directions (as defined by FIG. 17(b)).

Example 3: Measurement of Vector Electrical and Magnetic Field Distribution

Figure 19:
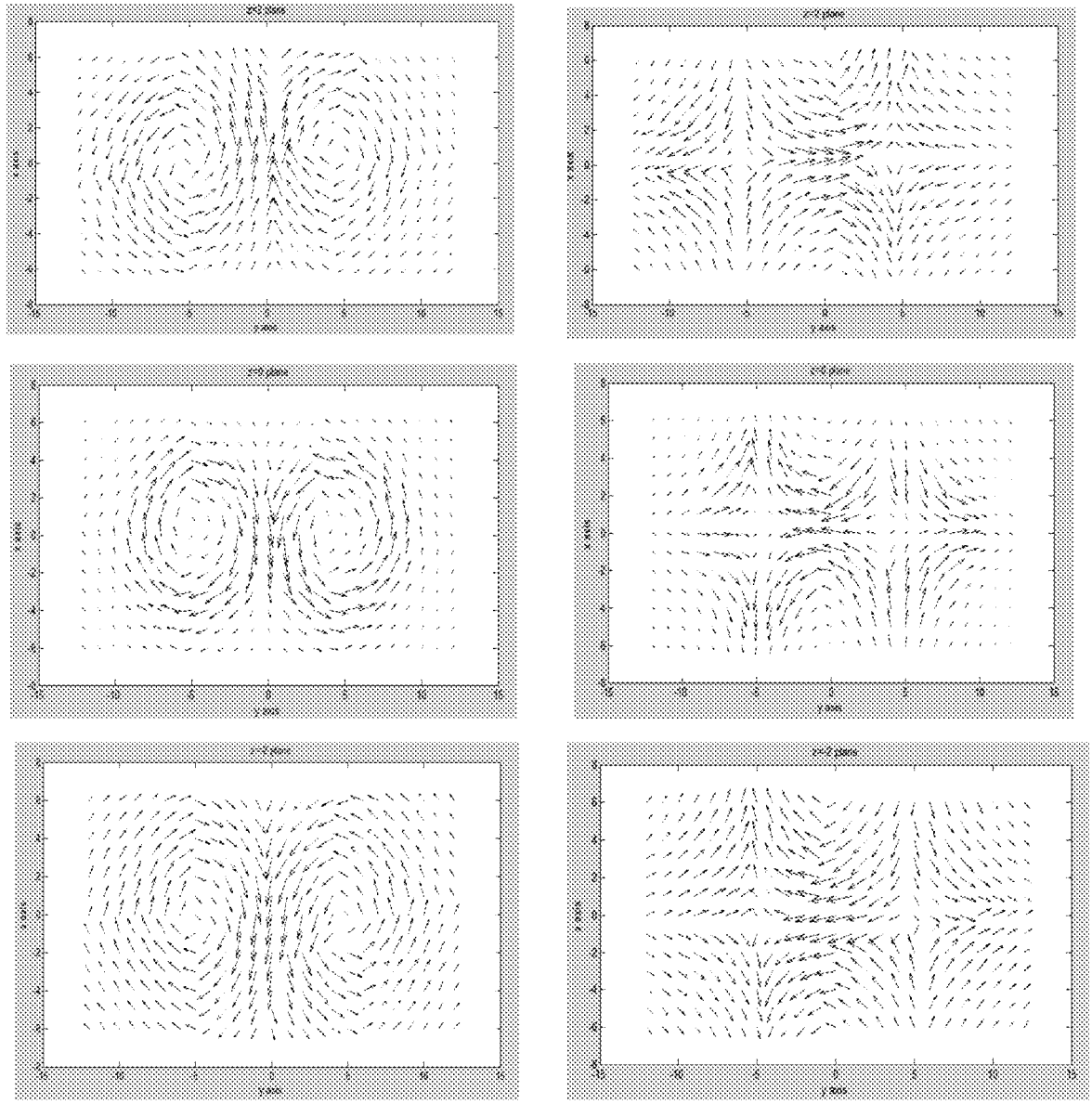
FIG. 19 illustrates sample data captured showing high accuracy measurements using TMS sensor probes and methods in accordance with certain aspects of the invention.

FIG. 19 illustrates test results from the simultaneous measurement of vector electrical and magnetic field distributions. These measurements are verified by measuring vector fields using the electrical field probes 300 configured in accordance with various aspects of the invention. The left column of FIG. 19 shows data of the measured 2-D vector electric field distributions. Likewise, the right column of FIG. 19 shows data of the 2-D vector magnetic field distributions at different planes away from the commercial Figure-8 TMS stimulator 420. The electrical and magnetic vector fields are orthogonal to each other at any location, as described by the Maxwell equation relationship in air.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense, Throughout this specification, unless the context equires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant, to indicate one or more of the item, element or step modified by the article.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A magnetic field sensor probe comprising:
   a field detector configured to measure a characteristic of a transcranial magnetic stimulation-induced electrical field induced by a magnetic field generator at a location of said field detector, said field detector further comprising a first coil formed of electrical conductive material and having a plurality of first coil turns, wherein at least a portion of said first coil is coiled around and encircles at least a portion of a second coil formed of magnetic material and having a plurality of second coil turns;
   a first electrical connection in electrical communication with said field detector;
   a second electrical connection in electrical communication with said field detector; and
   a processor in electrical communication with said second electrical connection, said processor having computer executable code stored thereon configured to:
   receive a signal from said field detector indicative of said measured characteristic; and
   process said signal to generate a human-readable depiction of at least a portion of a calculated transcranial magnetic stimulation-induced electrical field.

2. The magnetic field sensor probe of claim 1, further comprising a power source in electrical communication with said first electrical connection.

3. The magnetic field sensor probe of claim 1, wherein said field detector further comprises an electrical coil.

4. The magnetic field sensor probe of claim 3, wherein said processor is further configured to detect an envelope of a measured pulse field of said induced electrical field.

5. The magnetic field sensor probe of claim 1, wherein said signal received from said field detector further comprises an indication of a change in voltage in said first coil.

6. The magnetic field sensor probe of claim 1, further comprising a plurality of said field detectors.

7. A system for detecting and displaying characteristics of an electrical field induced by a magnetic field generator, comprising:
   the magnetic field generator;
   a magnetic field sensor probe, said magnetic field sensor probe further comprising:
     a field detector configured to measure a characteristic of a transcranial magnetic stimulation-induced electrical field induced by a magnetic field generator at a location of said field detector, said field detector further comprising a first coil formed of electrical conductive material and having a plurality of first coil turns, wherein at least a portion of said first coil is coiled around and encircles at least a portion of a second coil formed of magnetic material and having a plurality of second coil turns;
   a first electrical connection in electrical communication with said field detector;
   a second electrical connection in electrical communication with said field detector; and
   a processor in electrical communication with said second electrical connection, said processor having computer executable code stored thereon configured to:
     receive a signal from said field detector indicative of said measured characteristic; and
     process said signal to generate a human-readable depiction of at least a portion of a calculated transcranial magnetic stimulation-induced electrical field.

8. The system of claim 7, wherein said field detector further comprises an electrical coil.

9. The system of claim 7, wherein said signal received from said field detector further comprises an indication of a change in voltage in said first coil.

10. A method of calibrating an electrical field induced by a magnetic field generator, comprising the steps of:
    providing a magnetic field generator;
    causing said magnetic field generator to create a magnetic field;
    providing a magnetic field sensor probe, said magnetic field sensor probe further comprising:
      a field detector configured to measure a characteristic of a transcranial magnetic stimulation-induced electrical field induced by the magnetic field generator at a location of said field detector, said field detector further comprising a first coil formed of electrical conductive material and having a plurality of first coil turns, wherein at least a portion of said first coil is coiled around and encircles at least a portion of a second coil formed of magnetic material and having a plurality of second coil turns;
    a first electrical connection in electrical communication with said field detector;
    a second electrical connection in electrical communication with said field detector; and
    a processor in electrical communication with said second electrical connection, said processor having computer executable code stored thereon configured to:
      receive a signal from said field detector indicative of said measured characteristic; and process said signal to generate a human-readable depiction of at least a portion of a calculated transcranial magnetic stimulation-induced electrical field;

placing said magnetic field sensor probe in said magnetic field;

detecting said characteristic of said electrical field induced by said magnetic field generator; and modifying said transcranial magnetic stimulation-induced electrical field in response to said characteristic.

11. The method of claim 10, wherein said field detector further comprises an electrical coil.

12. The method of claim 10, wherein said signal received from said field detector further comprises an indication of a change in voltage in said first coil.

* * * * *